(12) United States Patent
Nhan et al.

(10) Patent No.: US 8,372,766 B2
(45) Date of Patent: *Feb. 12, 2013

(54) CONDUCTIVE WEBS

(75) Inventors: Davis-Dang H. Nhan, Appleton, WI (US); Duane Joseph Shukoski, Neenah, WI (US)

(73) Assignee: Kimberly-Clark Worldwide, inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/888,334

(22) Filed: Jul. 31, 2007

(65) Prior Publication Data

US 2009/0036012 A1 Feb. 5, 2009

(51) Int. Cl.
*D04H 1/00* (2006.01)
*D21H 27/00* (2006.01)

(52) U.S. Cl. ........ 442/414; 442/332; 442/334; 442/335; 442/341; 442/354; 442/415; 428/299.1; 428/367; 428/408; 162/129

(58) Field of Classification Search ............ 442/21, 442/198, 265, 273, 341, 349, 354, 408; 604/358–402; 423/447.1; 162/111, 123–131, 162/138, 141–150, 218–224
See application file for complete search history.

(56) References Cited

U.S. PATENT DOCUMENTS

| | | | |
|---|---|---|---|
| 3,120,342 A | 2/1964 | Geiger | |
| 3,265,557 A | 8/1966 | De Fries et al. | |
| 3,367,851 A * | 2/1968 | Filreis et al. | 205/52 |
| 3,556,932 A | 1/1971 | Costa et al. | |
| 3,556,933 A | 1/1971 | Williams et al. | |
| 3,585,104 A | 6/1971 | Kleinert | |
| 3,700,623 A | 10/1972 | Keim | |
| 3,772,076 A | 11/1973 | Keim | |
| 3,855,158 A | 12/1974 | Petrovich et al. | |
| 3,859,504 A | 1/1975 | Motokawa et al. | |
| 3,899,388 A | 8/1975 | Petrovich et al. | |
| 3,998,689 A | 12/1976 | Kitago et al. | |
| 4,032,607 A | 6/1977 | Schulz | |
| 4,129,528 A | 12/1978 | Petrovich et al. | |
| 4,147,586 A | 4/1979 | Petrovich et al. | |
| 4,222,921 A | 9/1980 | Van Eenam | |
| 4,256,801 A * | 3/1981 | Chuluda | 442/322 |
| 4,514,345 A | 4/1985 | Johnson et al. | |
| 4,528,239 A | 7/1985 | Trokhan | |
| 4,594,130 A | 6/1986 | Cheng et al. | |
| 4,606,790 A * | 8/1986 | Youngs et al. | 162/125 |

(Continued)

FOREIGN PATENT DOCUMENTS

| EP | 1674036 A1 | 6/2006 |
|---|---|---|
| GB | 2250121 * | 5/1992 |

(Continued)

OTHER PUBLICATIONS

Wet-laid definition, Textile Glossary, copyright 2001, Celanese Acetate.*

(Continued)

*Primary Examiner* — Jennifer A Steele
(74) *Attorney, Agent, or Firm* — Dority & Manning, P.A.

(57) ABSTRACT

Conductive nonwoven webs are disclosed. The nonwoven webs contain pulp fibers combined with conductive fibers. In one embodiment, the webs are made in a wetlaid tissue making process.

26 Claims, 8 Drawing Sheets

U.S. PATENT DOCUMENTS

| | | | |
|---|---|---|---|
| 4,704,166 A | | 11/1987 | Bach et al. |
| 4,728,395 A | * | 3/1988 | Boyd, Jr. .................. 162/138 |
| 4,793,898 A | | 12/1988 | Laamanen et al. |
| 4,820,170 A | * | 4/1989 | Redmond et al. .............. 439/66 |
| 4,940,464 A | | 7/1990 | Van Gompel et al. |
| 5,098,522 A | | 3/1992 | Smurkoski et al. |
| 5,129,988 A | | 7/1992 | Farrington, Jr. |
| 5,206,466 A | | 4/1993 | Inamiya |
| 5,260,171 A | | 11/1993 | Smurkoski et al. |
| 5,275,700 A | | 1/1994 | Trokhan |
| 5,324,579 A | | 6/1994 | Sassa et al. |
| 5,328,565 A | | 7/1994 | Rasch et al. |
| 5,334,289 A | | 8/1994 | Trokhan et al. |
| 5,429,686 A | | 7/1995 | Chiu et al. |
| 5,431,786 A | | 7/1995 | Rasch et al. |
| 5,486,166 A | | 1/1996 | Bishop et al. |
| 5,490,846 A | | 2/1996 | Ellis et al. |
| 5,496,624 A | | 3/1996 | Stelljes, Jr. et al. |
| 5,500,277 A | | 3/1996 | Trokhan et al. |
| 5,514,523 A | | 5/1996 | Trokhan et al. |
| 5,529,665 A | | 6/1996 | Kaun |
| 5,554,467 A | | 9/1996 | Trokhan et al. |
| 5,566,724 A | | 10/1996 | Trokhan et al. |
| 5,585,170 A | * | 12/1996 | Morris et al. ................ 442/398 |
| 5,595,628 A | | 1/1997 | Gordon et al. |
| 5,624,790 A | | 4/1997 | Trokhan et al. |
| 5,628,876 A | | 5/1997 | Ayers et al. |
| 5,656,132 A | | 8/1997 | Farrington, Jr. et al. |
| 5,672,248 A | | 9/1997 | Wendt et al. |
| 5,766,389 A | | 6/1998 | Brandon et al. |
| 5,808,554 A | | 9/1998 | Shuminov |
| 5,820,973 A | | 10/1998 | Dodge, II et al. |
| 6,096,169 A | | 8/2000 | Hermans et al. |
| 6,120,642 A | | 9/2000 | Lindsay et al. |
| 6,143,135 A | | 11/2000 | Hada et al. |
| 6,163,262 A | | 12/2000 | Wu |
| 6,197,154 B1 | | 3/2001 | Chen et al. |
| 6,224,714 B1 | | 5/2001 | Schroeder et al. |
| 6,274,667 B1 | | 8/2001 | Shannon et al. |
| 6,287,418 B1 | | 9/2001 | Schroeder et al. |
| 6,365,667 B1 | | 4/2002 | Shannon et al. |
| 6,474,367 B1 | | 11/2002 | Jayaraman et al. |
| 6,540,874 B1 | | 4/2003 | Ling-Chen |
| 6,645,190 B1 | | 11/2003 | Olson et al. |
| 6,736,935 B2 | | 5/2004 | Hermans et al. |
| 6,887,348 B2 | | 5/2005 | Hermans et al. |
| 6,953,516 B2 | | 10/2005 | Hermans et al. |
| 7,022,630 B2 | * | 4/2006 | Berman et al. ................ 442/365 |
| 7,157,134 B2 | | 1/2007 | Makela et al. |
| 2003/0155347 A1 | | 8/2003 | Oh et al. |
| 2005/0134162 A1 | | 6/2005 | Hiraki |
| 2006/0096115 A1 | | 5/2006 | Lee |
| 2006/0264796 A1 | | 11/2006 | Flick et al. |
| 2007/0024457 A1 | | 2/2007 | Long et al. |
| 2007/0035528 A1 | | 2/2007 | Hodge |
| 2007/0142799 A1 | | 6/2007 | Ales et al. |
| 2007/0295465 A1 | * | 12/2007 | Dyer et al. .................... 162/111 |

FOREIGN PATENT DOCUMENTS

| | | | |
|---|---|---|---|
| JP | 2004306389 A | * | 11/2004 |
| JP | 2004342509 A | | 12/2004 |
| WO | WO 9934057 A1 | | 7/1999 |
| WO | WO 0037009 A2 | | 6/2000 |
| WO | WO 0066835 A1 | | 11/2000 |
| WO | WO 0216920 A2 | | 2/2002 |

OTHER PUBLICATIONS

PCT/IB2008/052559 International Search Report, Jan. 30, 2009.

Hoon, S.R. et al., "Time-dependent resistivity in carbon fibre sheets", *Journal of Materials Science 20*, pp. 3311-3319, 1985.

Jang, Joon and S.K. Ryu, "Physical property and electrical conductivity of electroless Ag-plated carbon fiber-reinforced paper", *Journal of Materials Processing Technology 180*, pp. 66-73, 2006.

Van Heest, Cara, "Electrolux, Kimberly Clark and the Printed Electronics Uptake", *Printed Electronics World*-http://www.printedelectronicsworld.com/articles/electrolux_kimberly_clark_and_the_printed_electronics_uptake_00002094.asp, Mar. 10, 2010.

* cited by examiner

CONDUCTIVE WEBS

BACKGROUND

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

The absorbent core can be made of, for instance, superabsorbent particles. Many absorbent articles, especially those sold under the tradename HUGGIES™ by the Kimberly-Clark Corporation, are so efficient at absorbing liquids that it is sometimes difficult to tell whether or not the absorbent article has been insulted with a body fluid.

Accordingly, various types of moisture or wetness indicators have been suggested for use in absorbent articles. The wetness indicators may include alarm devices that are designed to assist parents or attendants identify a wet diaper condition early on. The devices can produce an audible signal.

In the past, for instance, wetness indicators have included an open circuit incorporated into the absorbent article that is attached to a power supply and an alarm device. When a conductive substance, such as urine, is detected in the absorbent article, the open circuit becomes closed causing the alarm device to activate. The open circuit may comprise, for instance, two conductive elements that may be made from a metal wire or foil.

Problems have been experienced, however, in efficiently and reliability incorporating wetness indicators into absorbent articles at the process speeds at which absorbent articles are produced. Thus, a need exists for improved wetness sensors that can be easily incorporated into absorbent articles.

In addition, a need also exists for conductive elements for use in a wetness indicator that are made from non-metallic materials. Incorporating metallic components into an absorbent article, for instance, may cause various problems. For instance, once the absorbent articles are packaged, the absorbent articles are typically exposed to a metal detector to ensure that no metallic contaminants have accidentally been included in the package. Making the conductive elements of a wetness indicator from a metal, however, may cause a metal detector to indicate a false positive. The incorporation of metal conductive elements into an absorbent article may also cause problems when the wearer is attempting to pass through a security gate that also includes a metal detector.

SUMMARY

The present disclosure is generally directed to a conductive nonwoven web that may be used in numerous applications. For example, in one embodiment, the nonwoven web may be used to form conductive elements of a wetness sensing device incorporated into an absorbent article. In one embodiment, the conductive nonwoven web contains a substantial amount of pulp fibers combined with conductive fibers and is formed through a tissue making process. The resulting web, which may have many similar properties to a tissue web, can then be easily incorporated into an absorbent article during its manufacture for forming an open circuit within the article. For example, in one embodiment, two strips or zones of the conductive nonwoven web are incorporated into an absorbent article for forming an open circuit. When a conductive substance extends between the two strips or conductive zones, a signaling device may be activated that produces a signal for indicating the presence of the conductive substance.

In one embodiment, for instance, the nonwoven material of the present disclosure comprises a nonwoven base web containing pulp fibers in an amount of at least about 50% by weight. The nonwoven base web further comprises conductive fibers in an amount of at least 1% by weight, such as at least 3% by weight. For instance, the conductive fibers may be present in the nonwoven base web in an amount sufficient for the base web to be conductive in at least one direction and in at least one zone. The conductive fibers incorporated into the base web may comprise, for instance, carbon fibers, metallic fibers, polymeric fibers containing a conductive material, or mixtures thereof.

In one embodiment, for instance, the nonwoven base web comprises a wet laid web made according to a tissue making process. The wet laid web, for instance, may comprise a through-air dried web, such as an uncreped through-air dried web.

In one embodiment, it may be desirable to incorporate and concentrate the conductive fibers within a certain layer of the base web. For instance, the base web may comprise a single ply web containing distinct layers of fibers. The base web, for instance, may include at least a first layer and a second layer. The conductive fibers may all be contained within the second layer.

In one particular embodiment, for instance, the single ply web can contain a third layer of fibers in addition to the first layer and the second layer. The second layer, containing the conductive fibers, may be positioned in between the first layer and the third layer. The first layer and the third layer, for instance, may comprise pulp fibers while the second layer may comprise a mixture of the conductive fibers and pulp fibers. In this manner, the base web maintains a soft and nonabrasive feel while containing conductive fibers in an amount sufficient for the base web to conduct electricity.

As described above, in one embodiment, the conductive fibers may comprise carbon fibers. The carbon fibers, for instance, may be formed from polyacrylonitrile. The carbon fibers may comprise chopped fibers that have a length of from about 1 mm to about 12 mm, such as from about 3 mm to about 6 mm. The fibers can have a diameter, for instance, from about 3 microns to about 15 microns, such as from about 5 microns to about 10 microns.

In addition to pulp fibers and conductive fibers, in one embodiment, the base web can further contain synthetic or polymeric fibers made from a thermoplastic material. By incorporating a thermoplastic fiber into the base web, the base web may be stronger and/or may be amenable to thermal bonding to other components, such as other webs and materials.

Although the nonwoven web described above has many different uses, in one embodiment, the web can be incorporated into an absorbent article. The absorbent article may comprise a chassis having an outer cover, an absorbent structure, and a liner. The absorbent structure, for instance, may be positioned in between the outer cover and the liner. Depending upon the article, the chassis may include a crotch region positioned in between a front region and a back region. The front region and the back region may define a waist region therebetween.

In accordance with the present disclosure, the absorbent article can further include a wetness sensing device that is activated when a conductive substance is detected in the absorbent article. The wetness sensing device includes at least one conductive element, such as a pair of spaced apart conductive elements in communication with a signaling device. The conductive elements may form an open circuit within the absorbent article and may be made from a conductive nonwoven web comprising a mixture of pulp fibers and conductive fibers. When a conductive substance (such as urine) is contacted with the conductive elements, the open circuit becomes closed causing the signaling device to produce a signal indicating the presence of the conductive substance.

The first and second conductive elements contained within the wetness sensing device may be separate and distinct strips or structures or may be contained in a single nonwoven web. For instance, in one embodiment, the nonwoven web may include conductive zones that comprise the first and second conductive elements.

As described, the conductive elements may comprise a wet laid web containing pulp fibers combined with carbon fibers. The nonwoven web may contain the conductive fibers in an amount sufficient so that at least one zone of the nonwoven web has a resistance of less than about 1500 Ohms/Square, such as less than about 100 Ohms/Square, such as less than about 30 Ohms/Square, such as less than about 10 Ohms/Square.

Other features and aspects of the present invention are discussed in greater detail below.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Figure 1:
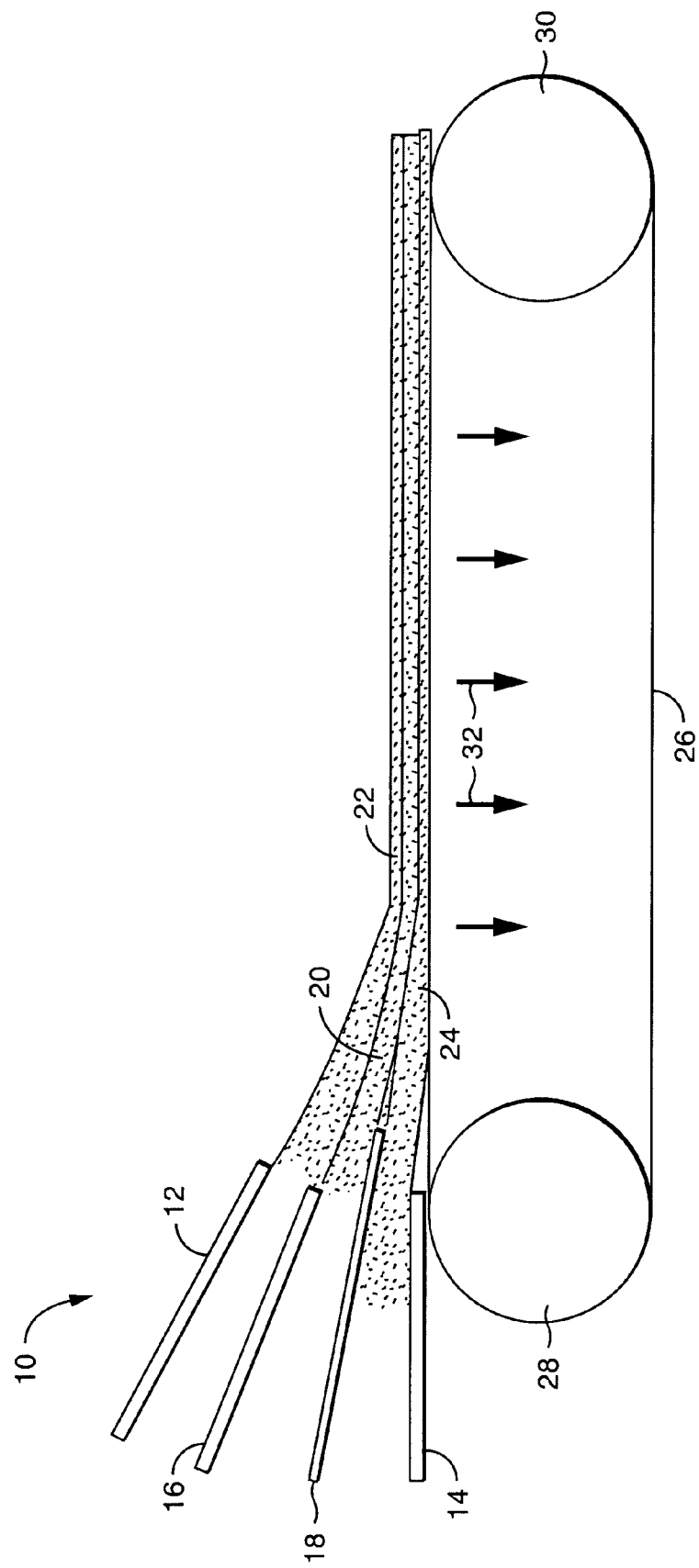
FIG. 1 is a side view of one embodiment of a process for forming multi-layered webs in accordance with the present disclosure.

Repeat use of reference characters in the present specification and drawings is intended to represent same or analogous features or elements of the present disclosure.

DETAILED DESCRIPTION

It is to be understood by one of ordinary skill in the art that the present discussion is a description of exemplary embodiments only, and is not intended as limiting the broader aspects of the present disclosure.

In general, the present disclosure is generally directed to nonwoven webs containing conductive fibers. The conductive fibers can be incorporated into the web, for instance, such that the web is electrically conductive in at least one zone. For instance, the nonwoven web can be made so that it is capable of carrying an electric current in the length direction, in the width direction, or in any suitable direction.

In accordance with the present disclosure, the conductive nonwoven webs can contain a substantial amount of pulp fibers and can be made using a tissue making process. For instance, in one embodiment, the conductive fibers can be combined with pulp fibers and water to form an aqueous suspension of fibers that is then deposited onto a porous surface for forming a conductive tissue web. The conductivity of the tissue web can be controlled by selecting particular conductive fibers, locating the fibers at particular locations within the web and by controlling various other factors and variables. In one embodiment, for instance, the conductive fibers incorporated into the nonwoven web comprise chopped carbon fibers.

Nonwoven webs made in accordance with the present disclosure may be used in numerous different applications. For instance, in one embodiment, the conductive nonwoven material may be incorporated into any suitable electronic device. For instance, the nonwoven web can be used as a fuel cell membrane, as a battery electrode, or may be used in printed electronics. For example, in one particular embodiment, the conductive fibers may form a patterned circuit within the base webs for any suitable end use application.

In one particular embodiment, for instance, the conductive nonwoven webs made in accordance with the present disclosure may be used to form wetness sensing devices within absorbent articles. The wetness sensing device, for instance, may be configured to emit a signal, such as an audible signal and/or a visible signal, when a conductive substance, such as urine or fecal matter, is detected in the absorbent article. In one embodiment, for instance, one or more nonwoven webs made in accordance with the present disclosure can be configured to form conductive elements within an absorbent article for creating an open circuit that is configured to close when a conductive substance is present in the article.

The absorbent article may be, for instance, a diaper, a training pant, an incontinence product, a feminine hygiene product, a medical garment, a bandage, and the like. Generally, the absorbent articles containing the open circuit are disposable meaning that they are designed to be discarded after a limited use rather than being laundered or otherwise restored for reuse.

The open circuit contained within the absorbent articles made from nonwoven webs of the present disclosure is configured to be attached to a signaling device. The signaling device can provide power to the open circuit while also including some type of audible and/or visible signal that indicates to the user the presence of a body fluid. Although the absorbent article itself is disposable, the signaling device may be reusable from article to article.

As described above, the base webs of the present disclosure are made by combining conductive fibers with pulp fibers to form nonwoven webs. In one embodiment, a tissue making process is used to form the webs.

The conductive fibers that may be used in accordance with the present disclosure can vary depending upon the particular application and the desired result. Conductive fibers that may be used to form the nonwoven webs include carbon fibers, metallic fibers, conductive polymeric fibers including fibers made from conductive polymers or polymeric fibers containing a conductive material, metal coated fibers, and mixtures thereof. Metallic fibers that may be used include, for instance, copper fibers, aluminum fibers, and the like. Polymeric fibers containing a conductive material include thermoplastic fibers coated with a conductive material or thermoplastic fibers impregnated or blended with a conductive material. For instance, in one embodiment, thermoplastic fibers may be used that are coated with silver.

The conductive fibers incorporated into the nonwoven material can have any suitable length and diameter. In one embodiment, for instance, the conductive fibers can have an aspect ratio of from about 100:1 to about 1,000:1.

The amount of conductive fibers contained in the nonwoven web can vary based on many different factors, such as the type of conductive fiber incorporated into the web and the ultimate end use of the web. The conductive fibers may be incorporated into the nonwoven web, for instance, in an amount from about 1% by weight to about 90% by weight, or even greater. For instance, the conductive fibers can be present in the nonwoven web in an amount from about 3% by weight to about 60% by weight, such as from about 3% by weight to about 20% by weight.

Carbon fibers that may be used in the present disclosure include fibers made entirely from carbon or fibers containing carbon in amounts sufficient so that the fibers are electrically conductive. In one embodiment, for instance, carbon fibers may be used that are formed from a polyacrylonitrile polymer. In particular, the carbon fibers are formed by heating, oxidizing, and carbonizing polyacrylonitrile polymer fibers. Such fibers typically have high purity and contain relatively high molecular weight molecules. For instance, the fibers can contain carbon in an amount greater than about 90% by weight, such as in an amount greater than 93% by weight, such as in an amount greater than about 95% by weight.

In order to form carbon fibers from polyacrylonitrile polymer fibers, the polyacrylonitrile fibers are first heated in an oxygen environment, such as air. While heating, cyano sites within the polyacrylonitrile polymer form repeat cyclic units of tetrahydropyridine. As heating continues, the polymer begins to oxidate. During oxidation, hydrogen is released causing carbon to form aromatic rings.

After oxidation, the fibers are then further heated in an oxygen starved environment. For instance, the fibers can be heated to a temperature of greater than about 1300° C., such as greater than 1400° C., such as from about 1300° C. to about 1800° C. During heating, the fibers undergo carbonization. During carbonization, adjacent polymer chains join together to form a lamellar, basal plane structure of nearly pure carbon.

Polyacrylonitrile-based carbon fibers are available from numerous commercial sources. For instance, such carbon fibers can be obtained from Toho Tenax America, Inc. of Rockwood, Tenn.

Other raw materials used to make carbon fibers are Rayon and petroleum pitch.

Of particular advantage, the formed carbon fibers can be chopped to any suitable length. In one embodiment of the present disclosure, for instance, chopped carbon fibers may be incorporated into the base web having a length of from about 1 mm to about 12 mm, such as from about 3 mm to about 6 mm. The fibers can have an average diameter of from about 3 microns to about 15 microns, such as from about 5 microns to about 10 microns. In one embodiment, for instance, the carbon fibers may have a length of about 3 mm and an average diameter of about 7 microns.

In one embodiment, the carbon fibers incorporated into the nonwoven base webs have a water soluble sizing. Sizing can be in the amount of 0.1-10% by weight. Water soluble sizings, can be, but not limited to, polyamide compounds, epoxy resin ester and poly(vinyl pyrrolidone). In this manner, the sizing is dissolved when mixing the carbon fibers in water to provide a good dispersion of carbon fibers in water prior to forming the nonwoven web.

In forming conductive nonwoven webs in accordance with the present disclosure, the above conductive fibers are combined with other fibers suitable for use in tissue making processes. The fibers combined with the conductive fibers may comprise any natural or synthetic cellulosic fibers including, but not limited to nonwoody fibers, such as cotton, abaca, kenaf, sabai grass, flax, esparto grass, straw, jute hemp, bagasse, milkweed floss fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898, issued Dec. 27, 1988 to Laamanen et al.; U.S. Pat. No. 4,594,130, issued Jun. 10, 1986 to Chang et al.; and U.S. Pat. No. 3,585,104. Useful fibers can also be produced by anthraquinone pulping, exemplified by U.S. Pat. No. 5,595,628 issued Jan. 21, 1997, to Gordon et al.

A portion of the fibers, such as up to 50% or less by dry weight, or from about 5% to about 30% by dry weight, can be synthetic fibers such as rayon, polyolefin fibers, polyester fibers, polyvinyl alcohol fibers, bicomponent sheath-core fibers, multi-component binder fibers, and the like. An exemplary polyethylene fiber is Pulpex®, available from Hercules, Inc. (Wilmington, Del.). Synthetic cellulose fiber types include rayon in all its varieties and other fibers derived from viscose or chemically-modified cellulose.

Incorporating thermoplastic fibers into the nonwoven web may provide various advantages and benefits. For example, incorporating thermoplastic fibers into the web may allow the webs to be thermally bonded to adjacent structures. For instance, the webs may be thermally bonded to other nonwoven materials, such as a diaper liner which may comprise, for instance, a spunbond web or a meltblown web.

Chemically treated natural cellulosic fibers can also be used such as mercerized pulps, chemically stiffened or crosslinked fibers, or sulfonated fibers. For good mechanical properties in using papermaking fibers, it can be desirable that the fibers be relatively undamaged and largely unrefined or only lightly refined. Mercerized fibers, regenerated cellulosic fibers, cellulose produced by microbes, rayon, and other cellulosic material or cellulosic derivatives can be used. Suitable fibers can also include recycled fibers, virgin fibers, or mixes thereof. In certain embodiments, the fibers can have a Canadian Standard Freeness of at least 200, more specifically at least 300, more specifically still at least 400, and most specifically at least 500.

Other papermaking fibers that can be used in the present disclosure include paper broke or recycled fibers and high yield fibers. High yield pulp fibers are those papermaking fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin. High yield fibers are well known for their stiffness in both dry and wet states relative to typical chemically pulped fibers.

In general, any process capable of forming a tissue web can be utilized in forming the conductive web. For example, a papermaking process of the present disclosure can utilize embossing, wet pressing, air pressing, through-air drying, uncreped through-air drying, hydroentangling, air laying, as well as other steps known in the art. The tissue web may be formed from a fiber furnish containing pulp fibers in an amount of at least 50% by weight, such as at least 60% by weight, such as at least 70% by weight, such as at least 80% by weight, such as at least 90% by weight.

The nonwoven webs can also be pattern densified or imprinted, such as the tissue sheets disclosed in any of the following U.S. Pat. No. 4,514,345 issued on Apr. 30, 1985, to Johnson et al.; U.S. Pat. No. 4,528,239 issued on Jul. 9, 1985, to Trokhan; U.S. Pat. No. 5,098,522 issued on Mar. 24, 1992; U.S. Pat. No. 5,260,171 issued on Nov. 9, 1993, to Smurkoski et al.; U.S. Pat. No. 5,275,700 issued on Jan. 4, 1994, to Trokhan; U.S. Pat. No. 5,328,565 issued on Jul. 12, 1994, to Rasch et al.; U.S. Pat. No. 5,334,289 issued on Aug. 2, 1994, to Trokhan et al.; U.S. Pat. No. 5,431,786 issued on Jul. 11, 1995, to Rasch et al.; U.S. Pat. No. 5,496,624 issued on Mar. 5, 1996, to Steltjes, Jr. et al.; U.S. Pat. No. 5,500,277 issued on Mar. 19, 1996, to Trokhan et al.; U.S. Pat. No. 5,514,523 issued on May 7, 1996, to Trokhan et al.; U.S. Pat. No. 5,554,467 issued on Sep. 10, 1996, to Trokhan et al.; U.S. Pat. No. 5,566,724 issued on Oct. 22, 1996, to Trokhan et al.; U.S. Pat. No. 5,624,790 issued on Apr. 29, 1997, to Trokhan et al.; and, U.S. Pat. No. 5,628,876 issued on May 13, 1997, to Ayers et al., the disclosures of which are incorporated herein by reference to the extent that they are non-contradictory herewith. Such imprinted tissue sheets may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits was deflected by an air pressure differential across the deflection conduit to form a lower-density pillow-like region or dome in the tissue sheet.

The tissue web can also be formed without a substantial amount of inner fiber-to-fiber bond strength. In this regard, the fiber furnish used to form the base web can be treated with a chemical debonding agent. The debonding agent can be added to the fiber slurry during the pulping process or can be added directly to the headbox. Suitable debonding agents that may be used in the present disclosure include cationic debonding agents such as fatty dialkyl quaternary amine salts, mono fatty alkyl tertiary amine salts, primary amine salts, imidazoline quaternary salts, silicone quaternary salt and unsaturated fatty alkyl amine salts. Other suitable debonding agents are disclosed in U.S. Pat. No. 5,529,665 to Kaun which is incorporated herein by reference. In particular, Kaun discloses the use of cationic silicone compositions as debonding agents.

In one embodiment, the debonding agent used in the process of the present disclosure is an organic quaternary ammonium chloride and, particularly, a silicone-based amine salt of a quaternary ammonium chloride. For example, the debonding agent can be PROSOFT® TQ1003, marketed by the Hercules Corporation. The debonding agent can be added to the fiber slurry in an amount of from about 1 kg per metric tonne to about 10 kg per metric tonne of fibers present within the slurry.

In an alternative embodiment, the debonding agent can be an imidazoline-based agent. The imidazoline-based debonding agent can be obtained, for instance, from the Witco Corporation. The imidazoline-based debonding agent can be added in an amount of between 2.0 to about 15 kg per metric tonne.

In one embodiment, the debonding agent can be added to the fiber furnish according to a process as disclosed in PCT Application having an International Publication No. WO 99/34057 filed on Dec. 17, 1998 or in PCT Published Application having an International Publication No. WO 00/66835 filed on Apr. 28, 2000, which are both incorporated herein by reference. In the above publications, a process is disclosed in which a chemical additive, such as a debonding agent, is adsorbed onto cellulosic papermaking fibers at high levels. The process includes the steps of treating a fiber slurry with an excess of the chemical additive, allowing sufficient residence time for adsorption to occur, filtering the slurry to remove unadsorbed chemical additives, and redispersing the filtered pulp with fresh water prior to forming a nonwoven web.

Wet and dry strength agents may also be applied or incorporated into the base sheet. As used herein, "wet strength agents" refer to materials used to immobilize the bonds between fibers in the wet state. Typically, the means by which fibers are held together in paper and tissue products involve hydrogen bonds and sometimes combinations of hydrogen bonds and covalent and/or ionic bonds. In the present invention, it may be useful to provide a material that will allow bonding of fibers in such a way as to immobilize the fiber-to-fiber bond points and make them resistant to disruption in the wet state.

Any material that when added to a tissue sheet or sheet results in providing the tissue sheet with a mean wet geometric tensile strength:dry geometric tensile strength ratio in excess of about 0.1 will, for purposes of the present invention, be termed a wet strength agent. Typically these materials are termed either as permanent wet strength agents or as "temporary" wet strength agents. For the purposes of differentiating permanent wet strength agents from temporary wet strength agents, the permanent wet strength agents will be defined as those resins which, when incorporated into paper or tissue products, will provide a paper or tissue product that retains more than 50% of its original wet strength after exposure to water for a period of at least five minutes. Temporary wet strength agents are those which show about 50% or less than, of their original wet strength after being saturated with water for five minutes. Both classes of wet strength agents find application in the present invention. The amount of wet strength agent added to the pulp fibers may be at least about 0.1 dry weight percent, more specifically about 0.2 dry weight percent or greater, and still more specifically from about 0.1 to about 3 dry weight percent, based on the dry weight of the fibers.

Permanent wet strength agents will typically provide a more or less long-term wet resilience to the structure of a tissue sheet. In contrast, the temporary wet strength agents will typically provide tissue sheet structures that had low density and high resilience, but would not provide a structure that had long-term resistance to exposure to water or body fluids.

The temporary wet strength agents may be cationic, nonionic or anionic. Such compounds include PAREZ™ 631 NC and PAREZ® 725 temporary wet strength resins that are cationic glyoxylated polyacrylamide available from Cytec Industries (West Paterson, N.J.). This and similar resins are described in U.S. Pat. No. 3,556,932, issued on Jan. 19, 1971, to Coscia et al. and U.S. Pat. No. 3,556,933, issued on Jan. 19, 1971, to Williams et al. Hercobond 1366, manufactured by Hercules, Inc., located at Wilmington, Del., is another commercially available cationic glyoxylated polyacrylamide that may be used in accordance with the present invention. Additional examples of temporary wet strength agents include dialdehyde starches such as Cobond® 1000 from National Starch and Chemical Company and other aldehyde containing polymers such as those described in U.S. Pat. No. 6,224,714, issued on May 1, 2001, to Schroeder et al.; U.S. Pat. No. 6,274,667, issued on Aug. 14, 2001, to Shannon et al.; U.S. Pat. No. 6,287,418, issued on Sep. 11, 2001, to Schroeder et al.; and, U.S. Pat. No. 6,365,667, issued on Apr. 2, 2002, to Shannon et al., the disclosures of which are herein incorporated by reference to the extent they are non-contradictory herewith.

Permanent wet strength agents comprising cationic oligomeric or polymeric resins can be used in the present invention. Polyamide-polyamine-epichlorohydrin type resins such as KYMENE 557H sold by Hercules, Inc., located at Wilmington, Del., are the most widely used permanent wet-strength agents and are suitable for use in the present invention. Such materials have been described in the following U.S. Pat. No.: 3,700,623, issued on Oct. 24, 1972, to Keim; U.S. Pat. No. 3,772,076, issued on Nov. 13, 1973, to Keim; U.S. Pat. No. 3,855,158, issued on Dec. 17, 1974, to Petrovich et al.; U.S. Pat. No. 3,899,388, issued on Aug. 12, 1975, to Petrovich et al.; U.S. Pat. No. 4,129,528, issued on Dec. 12, 1978, to Petrovich et al.; U.S. Pat. No. 4,147,586, issued on Apr. 3, 1979, to Petrovich et al.; and, U.S. Pat. No. 4,222,921, issued on Sep. 16, 1980, to van Eenam. Other cationic resins include polyethylenimine resins and aminoplast resins obtained by reaction of formaldehyde with melamine or urea. It can be advantageous to use both permanent and temporary wet strength resins in the manufacture of tissue products.

Dry strength agents are well known in the art and include but are not limited to modified starches and other polysaccharides such as cationic, amphoteric, and anionic starches and guar and locust bean gums, modified polyacrylamides, carboxymethylcellulose, sugars, polyvinyl alcohol, chitosans, and the like. Such dry strength agents are typically added to a fiber slurry prior to tissue sheet formation or as part of the creping package.

Additional types of chemicals that may be added to the nonwoven web include, but is not limited to, absorbency aids usually in the form of cationic, anionic, or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamin E, silicone, lotions in general and the like may also be incorporated into the finished products.

In general, the products of the present disclosure can be used in conjunction with any known materials and chemicals that are not antagonistic to its intended use. Examples of such materials include but are not limited to baby powder, baking soda, chelating agents, zeolites, perfumes or other odor-masking agents, cyclodextrin compounds, oxidizers, and the like. Of particular advantage, when carbon fibers are used as the conductive fibers, the carbon fibers also serve as odor absorbents. Superabsorbent particles, synthetic fibers, or films may also be employed. Additional options include dyes, optical brighteners, humectants, emollients, and the like.

Nonwoven webs made in accordance with the present disclosure can include a single homogeneous layer of fibers or may include a stratified or layered construction. For instance, the nonwoven web ply may include two or three layers of fibers. Each layer may have a different fiber composition. For example, referring to FIG. 1, one embodiment of a device for forming a multi-layered stratified pulp furnish is illustrated. As shown, a three-layered headbox 10 generally includes an upper head box wall 12 and a lower head box wall 14. Headbox 10 further includes a first divider 16 and a second divider 18, which separate three fiber stock layers.

Each of the fiber layers comprise a dilute aqueous suspension of fibers. The particular fibers contained in each layer generally depends upon the product being formed and the desired results. In one embodiment, for instance, middle layer 20 contains pulp fibers in combination with the conductive fibers. Outer layers 22 and 24, on the other hand, can contain only pulp fibers, such as softwood fibers and/or hardwood fibers.

Placing the conductive fibers within the middle layer 20 may provide various advantages and benefits. Placing the conductive fibers in the center of the web, for instance, can produce a conductive material that still has a soft feel on its surfaces. Concentrating the fibers in one of the layers of the web can also improve the conductivity of the material without having to add great amounts of the conductive fibers. In one embodiment, for instance, a three-layered web is formed in which each layer accounts for from about 15% to about 40% by weight of the web. The outer layers can be made of only pulp fibers or a combination of pulp fibers and thermoplastic fibers. The middle layer, on the other hand, may contain pulp fibers combined with conductive fibers. The conductive fibers may be contained in the middle layer in an amount from about 10% to about 90% by weight, such as in an amount from about 30% to about 70% by weight, such as in an amount from about 40% to about 60% by weight.

An endless traveling forming fabric 26, suitably supported and driven by rolls 28 and 30, receives the layered papermaking stock issuing from headbox 10. Once retained on fabric 26, the layered fiber suspension passes water through the fabric as shown by the arrows 32. Water removal is achieved by combinations of gravity, centrifugal force and vacuum suction depending on the forming configuration.

Forming multi-layered paper webs is also described and disclosed in U.S. Pat. No. 5,129,988 to Farrington, Jr., which is incorporated herein by reference.

Figure 2:
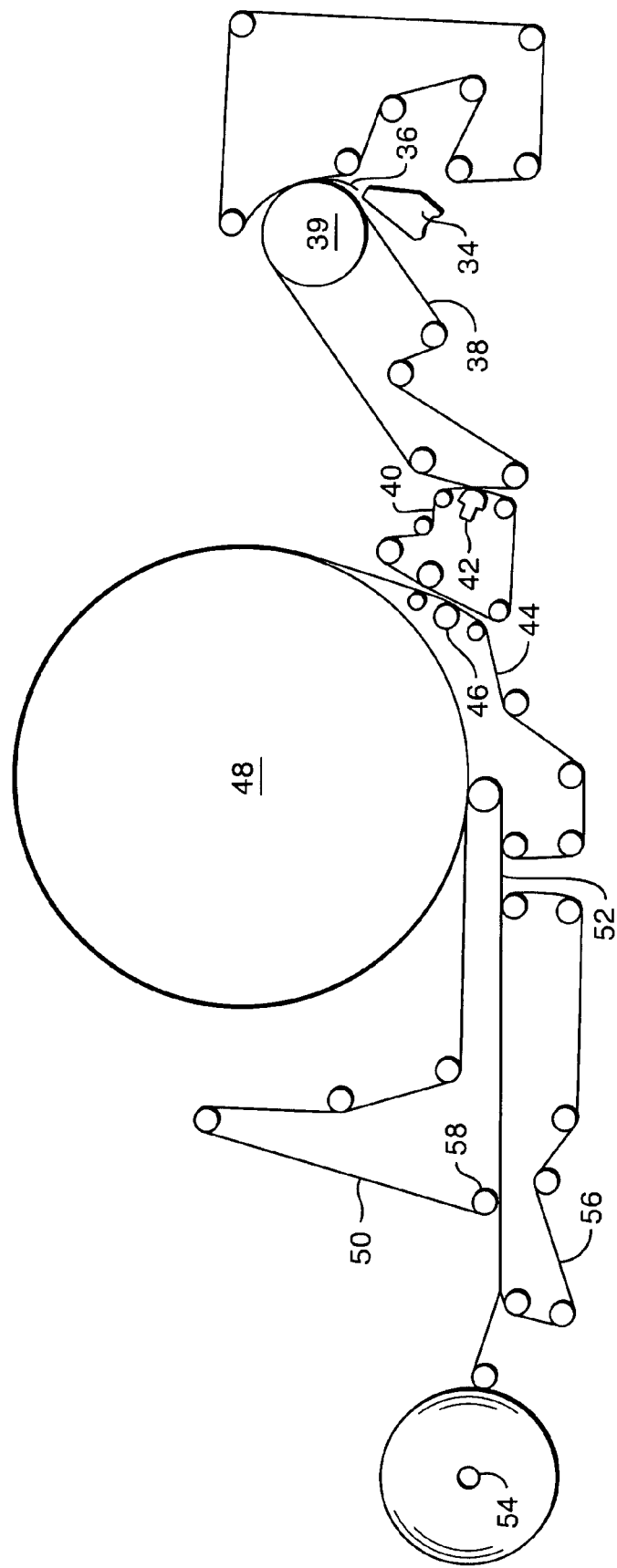
FIG. 2 is a side view of one embodiment of a process for forming uncreped through-air dried webs in accordance with the present disclosure.

Once the aqueous suspension of fibers is formed into a nonwoven web, the web may be processed using various techniques and methods. For example, referring to FIG. 2, shown is a method for making uncreped, throughdried tissue sheets. In one embodiment, it may be desirable to form the nonwoven web using an uncreped, through-air drying process. It was found that creping the nonwoven web during formation may cause damage to the conductive fibers by destroying the network of conductive fibers within the nonwoven web. Thus, the nonwoven web becomes non-conductive.

For simplicity, the various tensioning rolls schematically used to define the several fabric runs are shown, but not numbered. It will be appreciated that variations from the apparatus and method illustrated in FIG. 2 can be made without departing from the general process. Shown is a twin wire former having a papermaking headbox 34, such as a layered headbox, which injects or deposits a stream 36 of an aqueous suspension of papermaking fibers onto the forming fabric 38 positioned on a forming roll 39. The forming fabric serves to support and carry the newly-formed wet web downstream in the process as the web is partially dewatered to a consistency of about 10 dry weight percent. Additional dewatering of the wet web can be carried out, such as by vacuum suction, while the wet web is supported by the forming fabric.

The wet web is then transferred from the forming fabric to a transfer fabric 40. In one optional embodiment, the transfer fabric can be traveling at a slower speed than the forming fabric in order to impart increased stretch into the web. This is commonly referred to as a "rush" transfer. The relative speed difference between the two fabrics can be from 0-15 percent, more specifically from about 0-8 percent. Transfer is preferably carried out with the assistance of a vacuum shoe 42 such that the forming fabric and the transfer fabric simultaneously converge and diverge at the leading edge of the vacuum slot.

The web is then transferred from the transfer fabric to the throughdrying fabric 44 with the aid of a vacuum transfer roll 46 or a vacuum transfer shoe, optionally again using a fixed gap transfer as previously described. The throughdrying fabric can be traveling at about the same speed or a different speed relative to the transfer fabric. If desired, the throughdrying fabric can be run at a slower speed to further enhance stretch. Transfer can be carried out with vacuum assistance to ensure deformation of the sheet to conform to the throughdrying fabric, thus yielding desired bulk and appearance if desired. Suitable throughdrying fabrics are described in U.S. Pat. No. 5,429,686 issued to Kai F. Chiu et al. and U.S. Pat. No. 5,672,248 to Wendt, et al. which are incorporated by reference.

In one embodiment, the throughdrying fabric provides a relatively smooth surface. Alternatively, the fabric can contain high and long impression knuckles.

The side of the web contacting the throughdrying fabric is typically referred to as the "fabric side" of the nonwoven web. The fabric side of the web, as described above, may have a shape that conforms to the surface of the throughdrying fabric after the fabric is dried in the throughdryer. The opposite side of the paper web, on the other hand, is typically referred to as the "air side". The air side of the web is typically smoother than the fabric side during normal throughdrying processes.

The level of vacuum used for the web transfers can be from about 3 to about 15 inches of mercury (75 to about 380 millimeters of mercury), preferably about 5 inches (125 millimeters) of mercury. The vacuum shoe (negative pressure) can be supplemented or replaced by the use of positive pressure from the opposite side of the web to blow the web onto the next fabric in addition to or as a replacement for sucking it onto the next fabric with vacuum. Also, a vacuum roll or rolls can be used to replace the vacuum shoe(s).

While supported by the throughdrying fabric, the web is finally dried to a consistency of about 94 percent or greater by the throughdryer 48 and thereafter transferred to a carrier fabric 50. The dried basesheet 52 is transported to the reel 54 using carrier fabric 50 and an optional carrier fabric 56. An optional pressurized turning roll 58 can be used to facilitate transfer of the web from carrier fabric 50 to fabric 56. Suitable carrier fabrics for this purpose are Albany International 84M or 94M and Asten 959 or 937, all of which are relatively smooth fabrics having a fine pattern. Although not shown, reel calendering or subsequent off-line calendering can be used to improve the smoothness and softness of the basesheet. Calendering the web may also cause the conductive fibers to orient in a certain plane or in a certain direction. For instance, in one embodiment, the web can be calendered in order to cause primarily all of the conductive fibers to lie in the X-Y plane and not in the Z direction. In this manner, the conductivity of the web can be improved while also improving the softness of the web.

In one embodiment, the nonwoven web 52 is a web which has been dried in a flat state. For instance, the web can be formed while the web is on a smooth throughdrying fabric. Processes for producing uncreped throughdried fabrics are, for instance, disclosed in U.S. Pat. No. 5,672,248 to Wendt, et al.; U.S. Pat. No. 5,656,132 to Farrington, et al.; U.S. Pat. No. 6,120,642 to Lindsay and Burazin; U.S. Pat. No. 6,096,169 to Hermans. et al.; U.S. Pat. No. 6,197,154 to Chen, et al.; and U.S. Pat. No. 6,143,135 to Hada, et al., all of which are herein incorporated by reference in their entireties.

In FIG. 2, a process is shown for producing uncreped through-air dried webs. It should be understood, however, that any suitable process or technique that does not use creping may be used to form the conductive nonwoven web.

Nonwoven webs made in accordance with the present disclosure can have various different properties and characteristics depending upon the application in which the webs are to be used and the desired results. For instance, the nonwoven web can have a basis weight of from about 15 gsm to about 200 gsm or greater. For instance, the basis weight of the nonwoven web can be from about 15 gsm to about 100 gsm, such as from about 15 gsm to about 50 gsm.

If desired, the nonwoven web can be made with a relatively high bulk. For instance, the bulk can be from about 2 cc/g to about 20 cc/g, such as from about 3 cc/g to about 10 cc/g.

The sheet "bulk" is calculated as the quotient of the caliper of a dry tissue sheet, expressed in microns, divided by the dry basis weight, expressed in grams per square meter. The resulting sheet bulk is expressed in cubic centimeters per gram. More specifically, the caliper is measured as the total thickness of a stack of ten representative sheets and dividing the total thickness of the stack by ten, where each sheet within the stack is placed with the same side up. Caliper is measured in accordance with TAPPI test method T411 om-89 "Thickness (caliper) of Paper, Paperboard, and Combined Board" with Note 3 for stacked sheets. The micrometer used for carrying out T411 om-89 is an Emveco 200-A Tissue Caliper Tester available from Emveco, Inc., Newberg, Oreg. The micrometer has a load of 2.00 kilo-Pascals (132 grams per square inch), a pressure foot area of 2500 square millimeters, a pressure foot diameter of 56.42 millimeters, a dwell time of 3 seconds and a lowering rate of 0.8 millimeters per second.

The conductivity of the nonwoven web can also vary depending upon the type of conductive fibers incorporated into the web, the amount of conductive fibers incorporated into the web, and the manner in which the conductive fibers are positioned, concentrated or oriented in the web. In one embodiment, for instance, the nonwoven web can have a resistance of less than about 1500 Ohms/square, such as less than about 100 Ohms/square, such as less than about 10 Ohms/square.

The conductivity of the sheet is calculated as the quotient of the resistant measurement of a sheet, expressed in Ohms, divided by the ratio of the length to the width of the sheet. The resulting resistance of the sheet is expressed in Ohms per square. More specifically, the resistance measurement is in accordance with ASTM F1896-98 "Test Method for Determining the Electrical Resistivity of a Printed Conductive Material". The resistance measuring device (or Ohm meter) used for carrying out ASTM F1896-98 is a Fluke multimeter (model 189) equipped with Fluke alligator clips (model AC120); both are available from Fluke Corporation, Everett, Wash.

The resulting conductive web made in accordance with the present disclosure may be used alone as a single ply product or can be combined with other webs or films to form a multi-ply product. In one embodiment, the conductive nonwoven web may be combined with other tissue webs to form a 2-ply product or a 3-ply product. The other tissue webs, for instance, may be made entirely from pulp fibers and can be made according to any of the processes described above.

In an alternative embodiment, the conductive nonwoven web made according to the present disclosure may be laminated using an adhesive or otherwise to other nonwoven or polymeric film materials. For instance, in one embodiment, the conductive nonwoven web may be laminated to a meltblown web and/or a spunbond web that are made from polymeric fibers, such as polypropylene fibers. As described above, in one embodiment, the conductive nonwoven web can contain synthetic fibers. In this embodiment, the nonwoven web may be bonded to an opposing web containing synthetic fibers such as a meltblown web or spunbond web.

Incorporating the conductive nonwoven web into a multi-ply product may provide various advantages and benefits. For instance, the resulting multi-ply product may have better strength, may be softer, and/or may have better liquid wicking properties.

In one embodiment, the conductive fibers may be contained within the nonwoven web so as to form distinct zones of conductivity. For instance, in one embodiment, a head box may be used that instead of or in addition to separating the fibers vertically as shown in FIG. 1, the head box may be designed to also separate the fibers horizontally. In this manner, conductive fibers may only be contained in certain zones along the length (machine direction) of the web. The conductive zones may be separated by non-conductive zones that only contain non-conductive materials such as pulp fibers.

Figure 8:
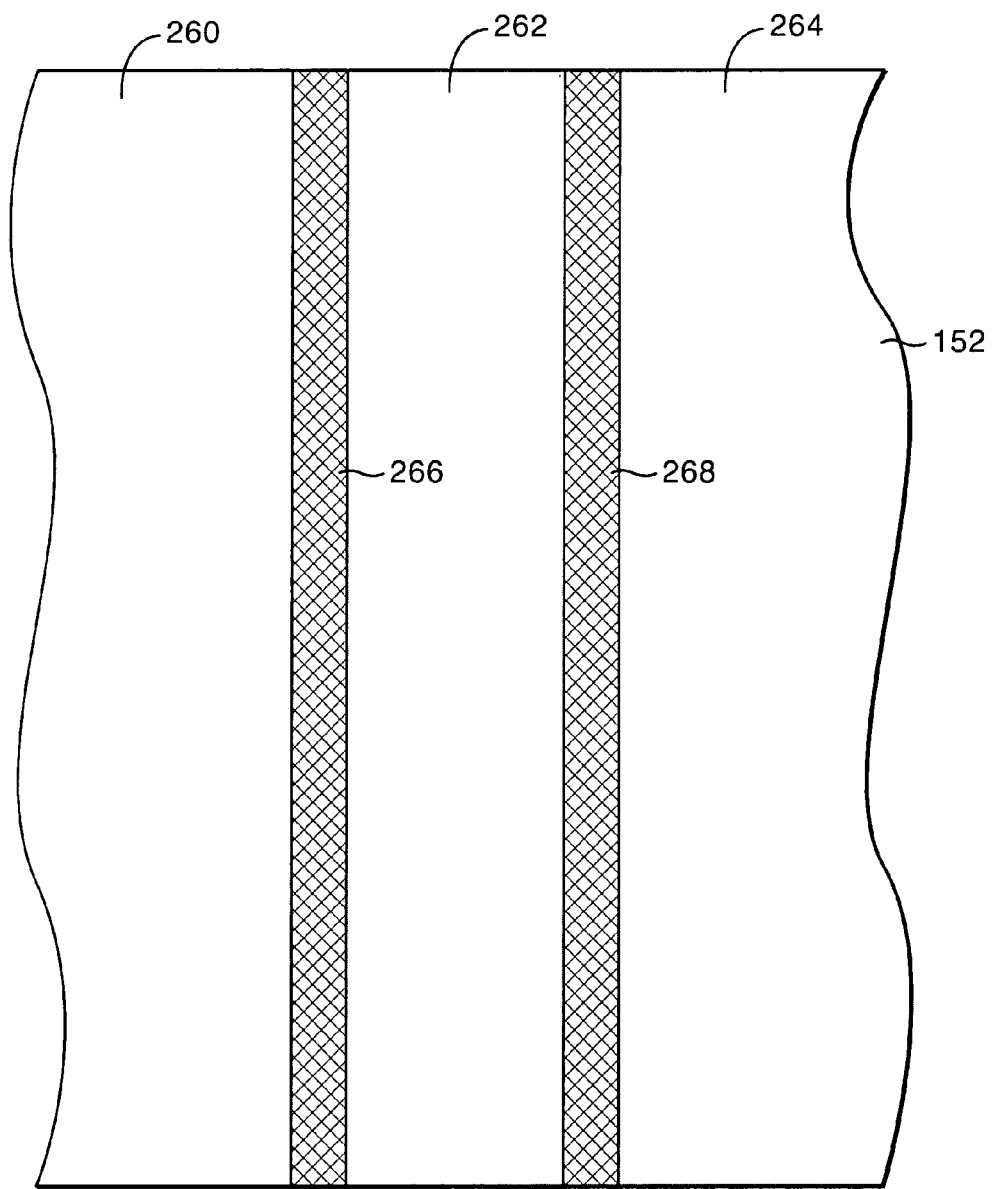
FIG. 8 is a perspective view of one embodiment of a conductive nonwoven web made in accordance with the present disclosure including different zones of conduction.

For instance, as shown in FIG. 8, a conductive nonwoven web 152 made in accordance with the present disclosure is shown. In this embodiment, conductive zones 266 and 268 have been formed into the web in the length direction. As shown in FIG. 8, the conductive zones 266 and 268 can be surrounded by non-conductive zones 260, 262 and 264.

As described above, nonwoven base webs made in accordance with the present disclosure may be used in numerous applications. For instance, the base webs may be used for their ability to conduct electric currents. In other embodiments, however, when using carbon fibers, the base webs may be used for their odor control properties. In still other embodiments, the conductive fibers may be present at the surface of the nonwoven web providing an abrasive product.

In one particular application, for instance, the conductive nonwoven web may be incorporated into a wetness sensing device that is configured to indicate the presence of a body fluid within an absorbent article. The wetness sensing device, for instance, may comprise an open circuit made from the conductive nonwoven material. The open circuit can be connected to a signaling device which is configured to emit an audible, visual or sensory signal when a conductive fluid closes the open circuit.

The particular targeted conductive fluid or body fluid may vary depending upon the particular type of absorbent article and the desired application. For instance, in one embodiment, the absorbent article comprises a diaper, a training pant, or the like and the wetness sensing device is configured to indicate the presence of urine. Alternatively, the wetness signaling device may be configured to indicate the presence of a metabolite that would indicate the presence of a diaper rash. For adult incontinence products and feminine hygiene products, on the other hand, the wetness signaling device may be configured to indicate the presence of a yeast or of a particular constituent in urine, such as a polysaccharide.

Figure 3:
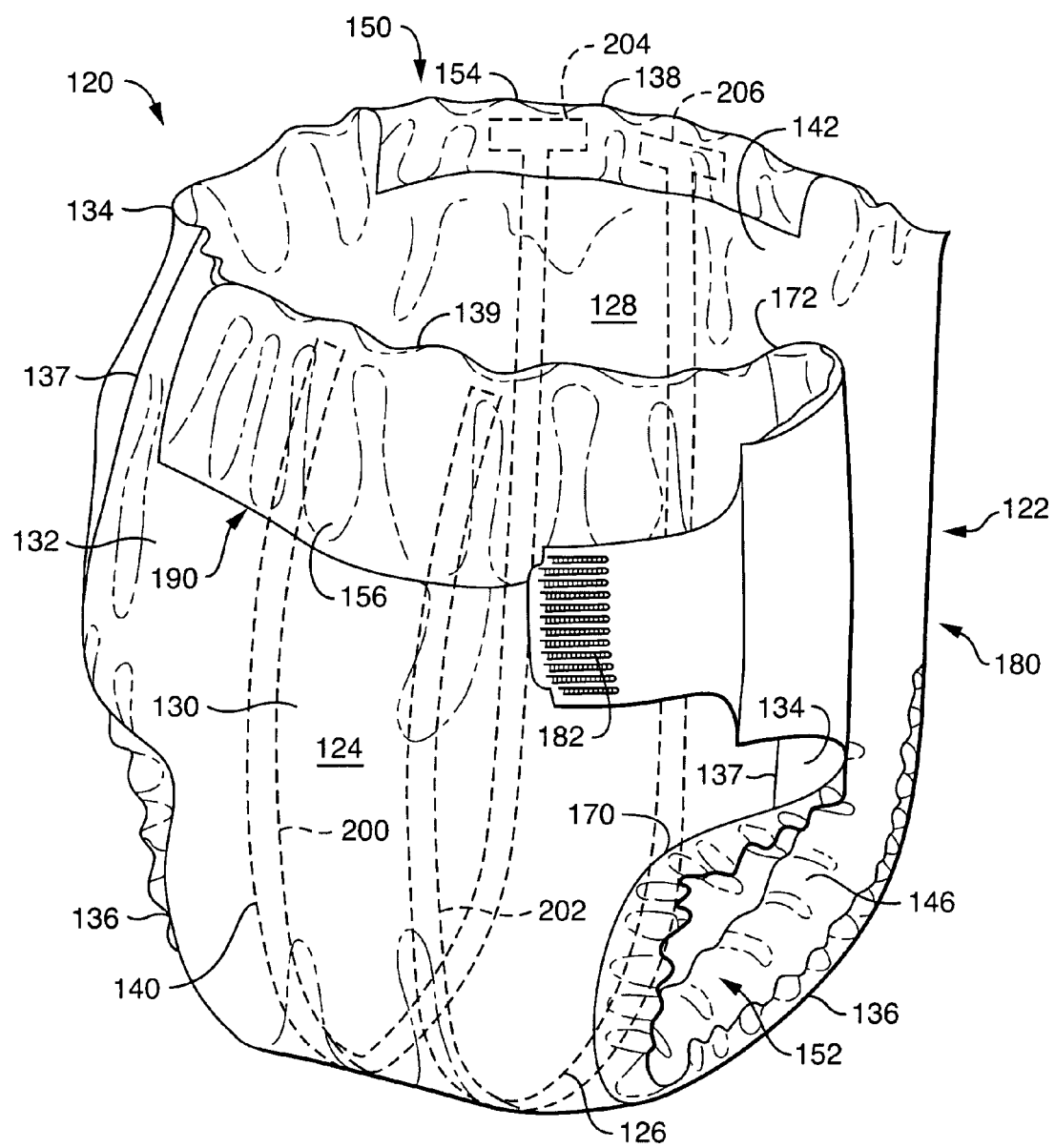
FIG. 3 is a rear perspective view of one embodiment of an absorbent article made in accordance with the present disclosure.
Figure 4:
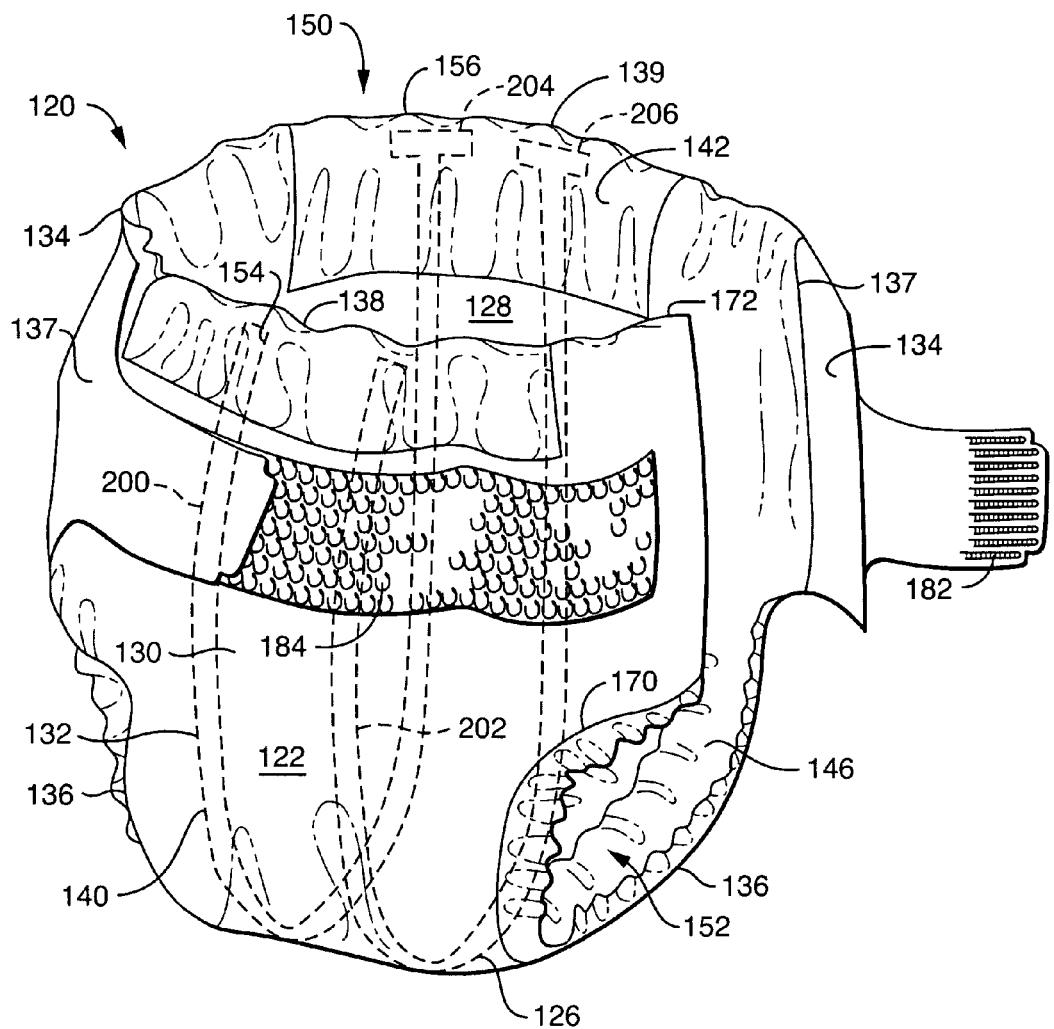
FIG. 4 is a front perspective view of the absorbent article illustrated in FIG. 3.

Referring to FIGS. 3 and 4, for exemplary purposes, an absorbent article 120 that may be made in accordance with the present invention is shown. The absorbent article 120 may or may not be disposable. It is understood that the present invention is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

By way of illustration only, various materials and methods for constructing absorbent articles such as the diaper 120 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 5:
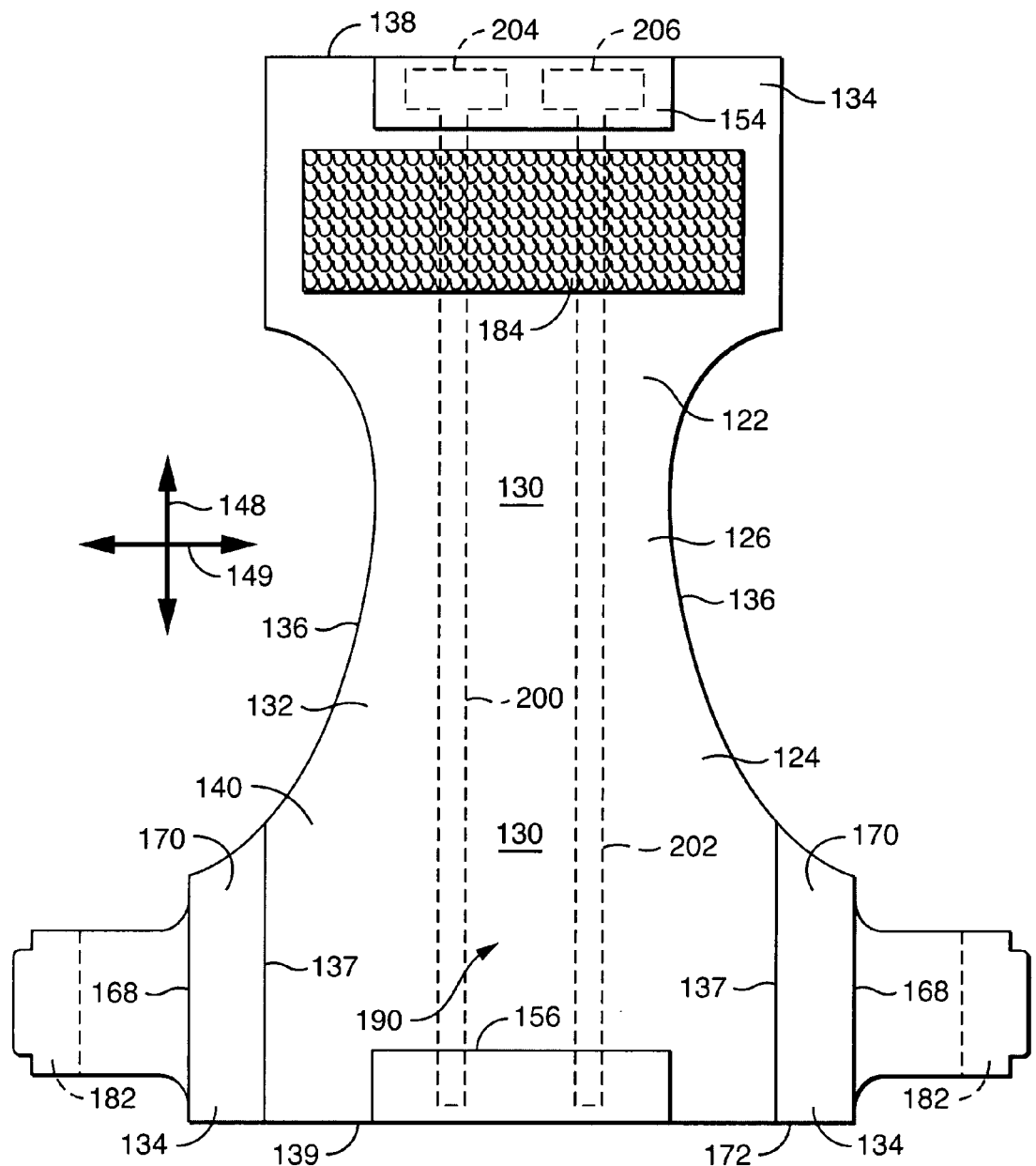
FIG. 5 is a plan view of the absorbent article shown in FIG. 3 with the article in an unfastened, unfolded and laid flat condition showing the surface of the article that faces away from the wearer.
Figure 6:
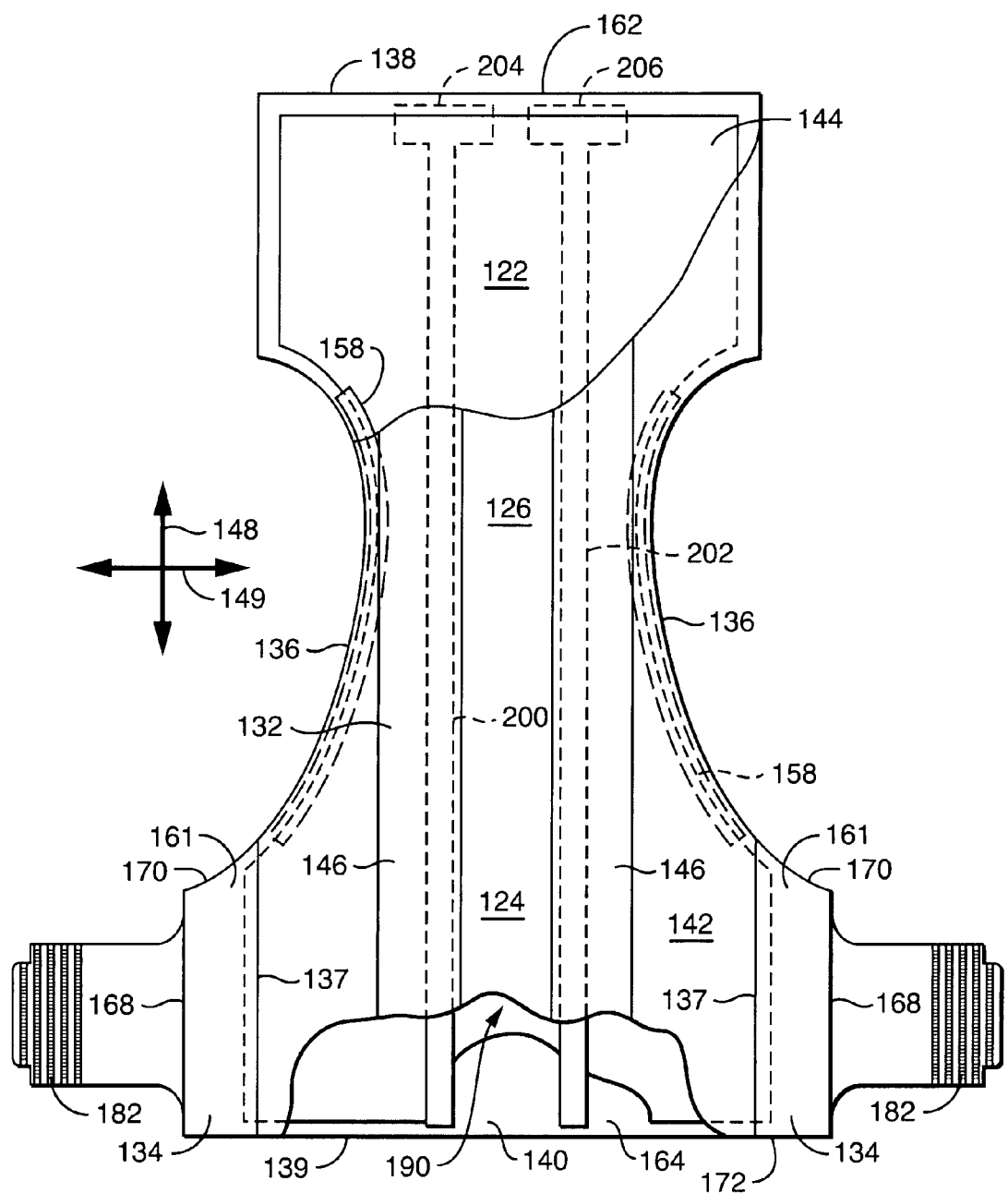
FIG. 6 is a plan view similar to FIG. 5 showing the surface of the absorbent article that faces the wearer when worn and with portions cut away to show underlying features.

A diaper 120 is representatively illustrated in FIG. 3 in a partially fastened condition. The diaper 120 shown in FIGS. 3 and 4 is also represented in FIGS. 5 and 6 in an opened and unfolded state. Specifically, FIG. 5 is a plan view illustrating the exterior side of the diaper 120, while FIG. 6 illustrates the interior side of the diaper 120. As shown in FIGS. 5 and 6, the diaper 120 defines a longitudinal direction 148 that extends from the front of the article when worn to the back of the article. Opposite to the longitudinal direction 148 is a lateral direction 149.

The diaper 120 defines a pair of longitudinal end regions, otherwise referred to herein as a front region 122 and a back region 124, and a center region, otherwise referred to herein as a crotch region 126, extending longitudinally between and interconnecting the front and back regions 122, 124. The diaper 120 also defines an inner surface 128 adapted in use (e.g., positioned relative to the other components of the article 120) to be disposed toward the wearer, and an outer surface 130 opposite the inner surface. The front and back regions 122, 124 are those portions of the diaper 120, which when worn, wholly or partially cover or encircle the waist or mid-lower torso of the wearer. The crotch region 126 generally is that portion of the diaper 120 which, when worn, is positioned between the legs of the wearer and covers the lower torso and crotch of the wearer. The absorbent article 120 has a pair of laterally opposite side edges 136 and a pair of longitudinally opposite waist edges, respectively designated front waist edge 138 and back waist edge 139.

The illustrated diaper 120 includes a chassis 132 that, in this embodiment, encompasses the front region 122, the back region 124, and the crotch region 126. Referring to FIGS. 3-6, the chassis 132 includes an outer cover 140 and a bodyside liner 142 (FIGS. 3 and 6) that may be joined to the outer cover 140 in a superimposed relation therewith by adhesives, ultrasonic bonds, thermal bonds or other conventional techniques. Referring to FIG. 6, the liner 142 may suitably be joined to the outer cover 140 along the perimeter of the chassis 132 to form a front waist seam 162 and a back waist seam 164. As shown in FIG. 6, the liner 142 may suitably be joined to the outer cover 140 to form a pair of side seams 161 in the front region 122 and the back region 124. The liner 142 can be generally adapted, i.e., positioned relative to the other components of the article 120, to be disposed toward the wearer's skin during wear of the absorbent article. The chassis 132 may further include an absorbent structure 144 particularly shown in FIG. 6 disposed between the outer cover 140 and the bodyside liner 142 for absorbing liquid body exudates exuded by the wearer, and may further include a pair of containment flaps 146 secured to the bodyside liner 142 for inhibiting the lateral flow of body exudates.

The elasticized containment flaps 146 as shown in FIG. 6 define a partially unattached edge which assumes an upright configuration in at least the crotch region 126 of the diaper 120 to form a seal against the wearer's body. The containment flaps 146 can extend longitudinally along the entire length of the chassis 132 or may extend only partially along the length of the chassis. Suitable constructions and arrangements for the containment flaps 146 are generally well known to those skilled in the art and are described in U.S. Pat. No. 4,704,116 issued Nov. 3, 1987 to Enloe, which is incorporated herein by reference.

To further enhance containment and/or absorption of body exudates, the diaper 120 may also suitably include leg elastic members 158 (FIG. 6), as are known to those skilled in the art. The leg elastic members 158 can be operatively joined to the outer cover 140 and/or the bodyside liner 142 and positioned in the crotch region 126 of the absorbent article 120.

The leg elastic members 158 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 158 may include a plurality of dry-spun coalesced multifilament spandex elastomeric threads sold under the trade name LYCRA and available from Invista, Wilmington, Del., USA.

In some embodiments, the absorbent article 120 may further include a surge management layer (not shown) which may be optionally located adjacent the absorbent structure 144 and attached to various components in the article 120 such as the absorbent structure 144 or the bodyside liner 142 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 3-6, the absorbent article 120 further includes a pair of opposing elastic side panels 134 that are attached to the back region of the chassis 132. As shown particularly in FIGS. 3 and 4, the side panels 134 may be stretched around the waist and/or hips of a wearer in order to secure the garment in place. As shown in FIGS. 5 and 6, the elastic side panels are attached to the chassis along a pair of opposing longitudinal edges 137. The side panels 134 may be attached or bonded to the chassis 132 using any suitable bonding technique. For instance, the side panels 134 may be joined to the chassis by adhesives, ultrasonic bonds, thermal bonds, or other conventional techniques.

In an alternative embodiment, the elastic side panels may also be integrally formed with the chassis 132. For instance, the side panels 134 may comprise an extension of the bodyside liner 142, of the outer cover 140, or of both the bodyside liner 142 and the outer cover 140.

In the embodiments shown in the figures, the side panels 134 are connected to the back region of the absorbent article 120 and extend over the front region of the article when securing the article in place on a user. It should be understood, however, that the side panels 134 may alternatively be connected to the front region of the article 120 and extend over the back region when the article is donned.

With the absorbent article 120 in the fastened position as partially illustrated in FIGS. 3 and 4, the elastic side panels 134 may be connected by a fastening system 180 to define a 3-dimensional diaper configuration having a waist opening 150 and a pair of leg openings 152. The waist opening 150 of the article 120 is defined by the waist edges 138 and 139 which encircle the waist of the wearer.

In the embodiments shown in the figures, the side panels are releasably attachable to the front region 122 of the article 120 by the fastening system. It should be understood, however, that in other embodiments the side panels may be permanently joined to the chassis 132 at each end. The side panels may be permanently bonded together, for instance, when forming a training pant or absorbent swimwear.

The elastic side panels 134 each have a longitudinal outer edge 168, a leg end edge 170 disposed toward the longitudinal center of the diaper 120, and waist end edges 172 disposed toward a longitudinal end of the absorbent article. The leg end edges 170 of the absorbent article 120 may be suitably curved and/or angled relative to the lateral direction 149 to provide a better fit around the wearer's legs. However, it is understood that only one of the leg end edges 170 may be curved or angled, such as the leg end edge of the back region 124, or alternatively, neither of the leg end edges may be curved or angled, without departing from the scope of the present invention. As shown in FIG. 6, the outer edges 168 are generally parallel to the longitudinal direction 148 while the waist end edges 172 are generally parallel to the transverse axis 149. It should be understood, however, that in other embodiments the outer edges 168 and/or the waist edges 172 may be slanted or curved as desired. Ultimately, the side panels 134 are generally aligned with a waist region 190 of the chassis.

The fastening system 180 may include laterally opposite first fastening components 182 adapted for refastenable engagement to corresponding second fastening components 184. In the embodiment shown in the figures, the first fastening component 182 is located on the elastic side panels 134, while the second fastening component 184 is located on the front region 122 of the chassis 132. In one aspect, a front or outer surface of each of the fastening components 182, 184 includes a plurality of engaging elements. The engaging elements of the first fastening components 182 are adapted to repeatedly engage and disengage corresponding engaging elements of the second fastening components 184 to releasably secure the article 120 in its three-dimensional configuration.

The fastening components 182, 184 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 182 include hook fasteners and the second fastening components 184 include complementary loop fasteners. Alternatively, the first fastening components 182 may include loop fasteners and the second fastening components 184 may be complementary hook fasteners. In another aspect, the fastening components 182, 184 can be interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components 182, 184. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 182 are attached to the side panels 134 along the edges 168. In this embodiment, the fastening components 182 are not elastic or extendable. In other embodiments, however, the fastening components may be integral with the side panels 134. For example, the fastening components may be directly attached to the side panels 134 on a surface thereof.

In addition to possibly having elastic side panels, the absorbent article 120 may include various waist elastic members for providing elasticity around the waist opening. For example, as shown in the figures, the absorbent article 120 can include a front waist elastic member 154 and/or a back waist elastic member 156.

As described above, the present disclosure is particularly directed to incorporating a body fluid indicating system, such as a wetness sensing device into the absorbent article 120. In this regard, as shown in FIGS. 3-6, the absorbent article 120 includes a first conductive element 200 spaced from a second conductive element 202. In this embodiment, the conductive elements extend from the front region 122 of the absorbent article to the back region 124 without intersecting. In accordance with the present disclosure, the conductive elements 200 and 202 can be made from a conductive nonwoven material as described above. In the embodiment illustrated in FIG. 4, the conductive elements 200 and 202 comprise separate and distinct strips or sheets.

The first conductive element 200 does not intersect the second conductive element 202 in order to form an open circuit that may be closed, for instance, when a conductive fluid is positioned in between the conductive elements. In other embodiments, however, the first conductive element 200 and the second conductive element 202 may be connected to a sensor within the chassis. The sensor may be used to sense changes in temperature or may be used to sense the presence of a particular substance, such as a metabolite.

In the embodiment shown in FIG. 3, the conductive elements 200 and 202 extend the entire length of the absorbent article 120. It should be understood, however, that in other embodiments the conductive elements may extend only to the crotch region 126 or may extend to any particular place in the absorbent article where a body fluid is intended to be sensed.

The conductive elements 200 and 202 may be incorporated into the chassis 132 at any suitable location as long as the conductive elements are positioned so as to contact a body fluid that is absorbed by the absorbent article 120. In this regard, the conductive elements 200 and 202 generally lie inside the outer cover 140. In fact, in one embodiment, the conductive elements 200 and 202 may be attached or laminated to the inside surface of the outer cover 140 that faces the absorbent structure 144. Alternatively, however, the conductive elements 200 and 202 may be positioned on the absorbent structure 144 or positioned on the liner 142.

In order for the conductive elements 200 and 202 to be easily connected to a signaling device, the first conductive element 200 can include a first conductive pad member 204, while the second conductive element 202 can include a second conductive pad member 206. The pad members 204 and 206 are provided for making a reliable connection between the open circuit formed by the conductive elements and a signaling device that is intended to be installed on the chassis by the consumer.

The position of the conductive pad members 204 and 206 on the absorbent article 120 can vary depending upon where it is desired to mount the signaling device. For instance, in FIGS. 3, 5 and 6, the conductive pad members 204 and 206 are positioned in the front region 122 along the waist opening of the article. In FIG. 4, on the other hand, the conductive pad members 204 and 206 are positioned in the back region 24 along the waist opening of the article. It should be appreciated, however, that in other embodiments, the absorbent article 20 may include conductive pad members being positioned at each end of each conductive element 200 and 202. In this manner, a user can determine whether or not to install the signaling device on the front or the back of the article. In still other embodiments, it should be understood that the pad members may be located along the side of the article or towards the crotch region of the article.

Figure 7:
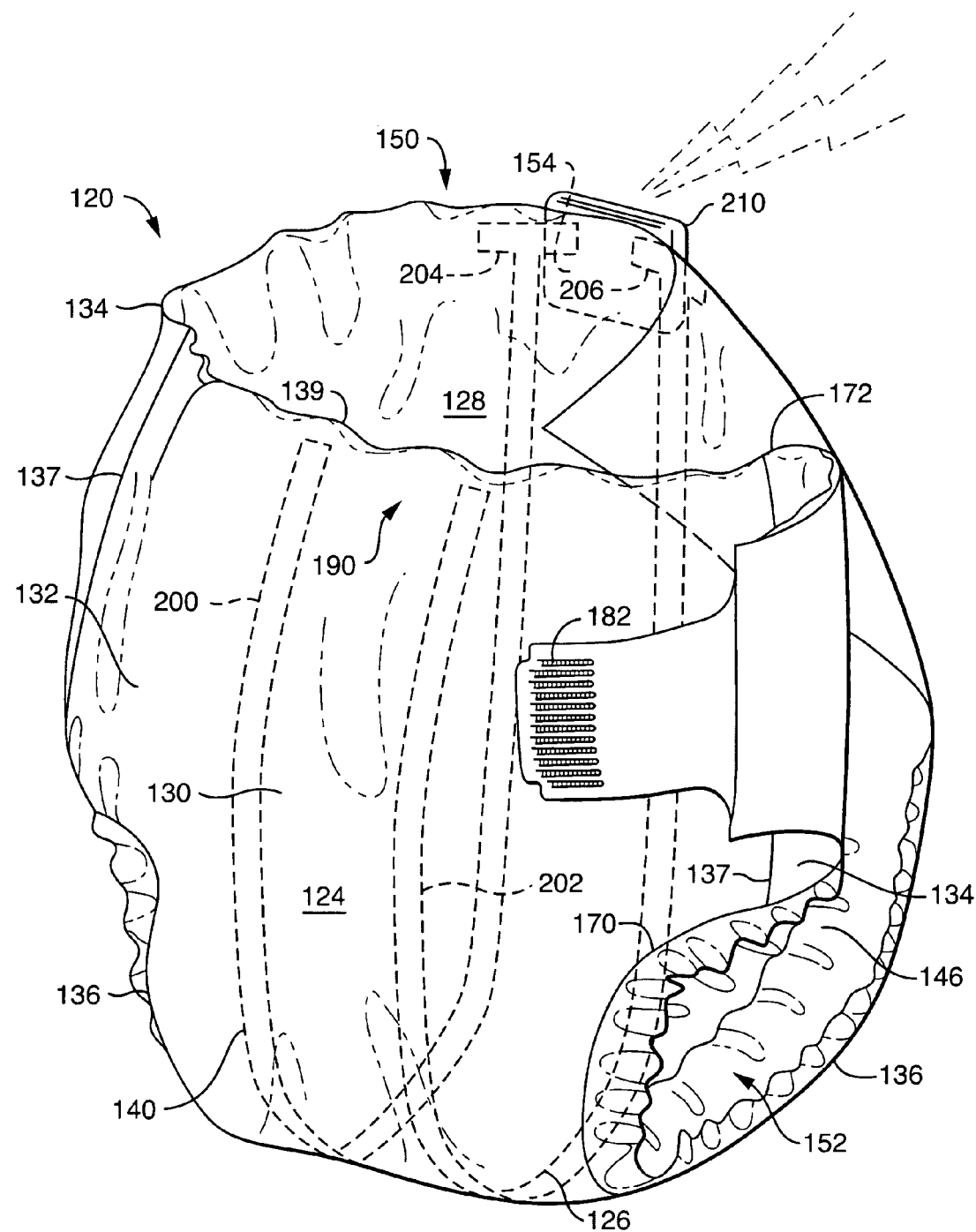
FIG. 7 is a perspective view of the embodiment shown in FIG. 3 further including one embodiment of a signaling device.

Referring to FIG. 7, for exemplary purposes, a signaling device 210 is shown attached to the conductive pad members 204 and 206. The signaling device 210 includes a pair of opposing terminals that are electrically connected to the corresponding conductive pad members. When a body fluid is present in the absorbent article 120, the open circuit formed by the conductive elements 200 and 202 is closed which, in turn, activates the signaling device 210.

The signaling device 210 can emit any suitable signal in order to indicate to the user that the circuit has been closed.

In FIG. 7, the conductive elements 200 and 202 are separate and distinct strips of material. In other embodiments, however, both of the conductive elements may be contained in a single nonwoven sheet. For instance, the conductive elements may be contained in a laminate that is incorporated into the absorbent article. In an alternative embodiment, the conductive elements may comprise conductive zones in a nonwoven web. For example, in one embodiment, the nonwoven material illustrated in FIG. 8 may be incorporated into the absorbent article illustrated in FIG. 3.

EXAMPLE

For exemplary purposes only, the following demonstrates the conductivity of base webs made in accordance with the present disclosure.

Uncreped, through-air dried wetlaid webs were made according to the present disclosure containing conductive carbon fibers. The uncreped, through-air drying process used was similar to the processes described in U.S. Pat. Nos. 6,887, 348, 6,736,935, 6,953,516, and 5,129,988 which are all incorporated herein by reference.

The tissue making process included a three-layer headbox that was used to form a wet web. More particularly, a three-layered web was produced containing northern bleached softwood kraft fibers (LL19 from Terrace Bay Pulp Inc.) in the two outer layers and a mixture of the above softwood fibers combined with carbon fibers in the middle layer. The carbon fiber used was TENAX 150 fibers obtained from Toho Tenax having a cut length of 3 mm. The fiber furnish used to produce the middle layer contained 50% by weight softwood fibers and 50% by weight carbon fibers. The consistency of the stock fed to the headbox was about 0.09 weight percent.

The three-layered sheet was formed on a twin-wire, suction form roll former using Lindsay 2164-B and Asten 867a forming fabrics. The newly-formed web was dewatered to a consistency of from about 20 to about 27% using vacuum suction from below the forming fabric before being transferred to a transfer fabric with about 10% rush transfer. The transfer fabric used was Appleton Wire T807-1 fabric. A vacuum shoe pulling about 6 to about 15 inches of mercury vacuum was used to transfer the web to the transfer fabric.

The web was then transferred to a throughdrying fabric which was also an Appleton Wire T807-1 fabric. The web was carried over the throughdryer operating at a temperature of about 350° F. (175° C.) and dried to a final dryness of from about 94 to about 98% consistency.

The resulting web was then tested for resistance. The following results were obtained:

|  | Sample 1 | Sample 2 |
| --- | --- | --- |
| Line Speed (FPM) | 1400 | 50 |
| Outer layer 1 | 35% softwood | 31% softwood |
| Middle layer | 15% carbon fiber | 19% carbon fiber |
|  | 15% softwood | 19% softwood |
| Outer layer 2 | 35% softwood | 31% softwood |
| Resistance (Ohms/square) | ~26 | ~13 |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A nonwoven material comprising:
a nonwoven base web containing pulp fibers in an amount of at least about 50% by weight, the nonwoven base web further comprising conductive fibers in an amount of at least about 1% by weight, the conductive fibers comprising carbon fibers;
wherein the carbon fibers contain carbon in an amount greater than about 90% by weight;
wherein the conductive fibers are present in the nonwoven base web so as to form at least one conductive zone and at least one nonconductive zone, the at least one conductive zone having a resistance of less than about 1500 Ohms/square;
wherein the nonwoven base web comprises a single ply web and is formed via depositing the fibers generally simultaneously in a wet laid process; and
wherein the at least one conductive zone and at least one nonconductive zone can be positioned either generally vertically or generally horizontally with respect to one another in the single ply web via the wet laid process, such that the at least one conductive zone is a mixture of pulp fibers and conductive fibers and the at least one nonconductive zone lacks conductive fibers; and
the nonwoven base web is calendared.

2. A nonwoven material as defined in claim 1, wherein the conductive fibers are present in the nonwoven base web in an amount sufficient for the material to be conductive in at least one direction.

3. A nonwoven material as defined in claim 1, wherein the carbon fibers are formed from a polyacrylonitrile.

4. A nonwoven material as defined in claim 1, wherein the carbon fibers have an average length of from about 3 mm to 6 mm.

5. A nonwoven material as defined in claim 1, wherein the nonwoven base web further contains thermoplastic fibers in addition to pulp fibers and conductive fibers.

6. A nonwoven material as defined in claim 1, wherein the conductive fibers are present in the base web such that the base web has multiple conductive zones.

7. A nonwoven material as defined in claim 6, wherein the conductive zones are separated by nonconductive zones.

8. A nonwoven material as defined in claim 1, wherein the conductive fibers have an aspect ratio of from about 100:1 to about 1,000:1.

9. A nonwoven material as defined in claim 1 wherein the base web comprises an uncreped through-air dried web.

10. A nonwoven material as defined in claim 1, wherein the nonwoven base web has a basis weight of from about 15 gsm to about 100 gsm.

11. A nonwoven material as defined in claim 1, wherein the conductive fibers comprise carbon fibers and the single ply web comprises an uncreped through-air dried web.

12. A nonwoven material as defined in claim 1, wherein the nonwoven material comprises a laminate, the nonwoven base web being laminated to at least one other layer of material, the other layer of material comprising a woven material, a nonwoven material, or a film.

13. A nonwoven material as defined in claim 12, wherein the at least one other material comprises a nonwoven web containing synthetic fibers.

14. A nonwoven material comprising:
a nonwoven base web comprising a single ply web containing layers of fibers wherein the nonwoven base web is formed via depositing the layers of fibers generally simultaneously in a wet laid process, the base web including at least a first layer of fibers and a second layer of fibers, the first layer containing pulp fibers, the second layer containing conductive fibers wherein the conductive fibers contain carbon in an amount greater than about 90% by weight, wherein the conductive fibers are present in the nonwoven base web so as to form at least one conductive zone and at least one nonconductive zone, the at least one conductive zone having a resistance of less than about 1500 Ohms/square;
wherein the base web further includes a third layer of fibers, the second layer being positioned in between the first layer and the third layer, the first layer and the third layer comprising essentially pulp fibers; and
wherein the conductive zone and nonconductive zone can be in different layers of fibers or contained in the same layer of fibers and the at least one conductive zone is a mixture of pulp fibers and conductive fibers and the at least one nonconductive zone lacks conductive fibers.

15. A nonwoven material as defined in claim 14, wherein the second layer contains pulp fibers combined with the conductive fibers, the conductive fibers being present in the base web in an amount of at least about 1% by weight.

16. A nonwoven material as defined in claim 14, wherein the second layer contains conductive fibers combined with pulp fibers, the conductive fibers comprising carbon fibers, the carbon fibers being present in the second layer in an amount from about 5% to about 90% by weight.

17. A nonwoven material as defined in claim 14, wherein the carbon fibers have an average length of from about 3 mm to 6 mm.

18. A nonwoven material as defined in claim 16, wherein the conductive fibers are present in the base web such that the base web has multiple conductive zones.

19. A nonwoven material as defined in claim 18, wherein the conductive zones are separated by nonconductive zones.

20. A nonwoven material as defined in claim 18, wherein the base web comprises an uncreped through-air dried web.

21. A nonwoven material as defined in claim 1, wherein the at least one conductive zone has a resistance of less than about 100 Ohms/square.

22. A nonwoven material as defined in claim 1, wherein the at least one conductive zone has a resistance of less than about 30 Ohms/square.

23. A nonwoven material as defined in claim 7, wherein the nonconductive zones have a resistance of greater than about 1500 Ohms/square.

24. A nonwoven material as defined in claim 19, wherein the nonconductive zones have a resistance of greater than about 1500 Ohms/square.

25. A nonwoven material comprising:
 a nonwoven base web containing pulp fibers in an amount of at least about 50% by weight, the nonwoven base web further comprising conductive fibers in an amount of at least about 1% by weight, the conductive fibers comprising carbon fibers;
 wherein the carbon fibers contain carbon in an amount greater than about 90% by weight;
 wherein the conductive fibers are present in the nonwoven base web so as to form at least two conductive zones and at least one nonconductive zone, each of the conductive zones having a resistance of less than about 1500 Ohms/square;
 wherein the nonwoven base web comprises a single ply web and is formed via depositing the fibers generally simultaneously in a wet laid process;
 wherein the at least one nonconductive zone is positioned between and separates the at least two conductive zones and the at least two conductive zones are mixtures of pulp fibers and conductive fibers and the at least one nonconductive zone lacks conductive fibers; and
 the nonwoven base web is calendared.

26. A nonwoven material as defined in claim 25 wherein there is at least three nonconductive zones; and
 wherein each conductive zone is positioned between at least two nonconductive zones.

* * * * *